(12) United States Patent
Graindorge et al.

(10) Patent No.: US 7,236,833 B2
(45) Date of Patent: Jun. 26, 2007

(54) MANAGING MEDICAL DATA OF AN ACTIVE IMPLANTABLE DEVICE SUCH AS A PACEMAKER, DEFIBRILLATOR, CARDIOVERTOR AND/OR MULTISITE DEVICE FOR A CARDIOLOGIST

(75) Inventors: Laurence Graindorge, Chatenay-Malabry (FR); Marcel Limousin, Paris (FR)

(73) Assignee: ELA Medical S.A.S., Montrouge (FR)

( * ) Notice: Subject to any disclaimer, the term of this patent is extended or adjusted under 35 U.S.C. 154(b) by 444 days.

(21) Appl. No.: 10/145,573

(22) Filed: May 13, 2002

(65) Prior Publication Data

US 2003/0013945 A1 Jan. 16, 2003

(30) Foreign Application Priority Data

May 15, 2001 (FR) .................................... 01 06374

(51) Int. Cl.
*A61N 1/08* (2006.01)
(52) U.S. Cl. ...................................................... 607/60
(58) Field of Classification Search ............ 607/30–32, 607/59–60; 128/903; 600/523
See application file for complete search history.

(56) References Cited

U.S. PATENT DOCUMENTS

| 4,531,527 | A | | 7/1985 | Reinhold, Jr. et al. | |
|---|---|---|---|---|---|
| 5,722,999 | A | * | 3/1998 | Snell | 607/32 |
| 5,833,623 | A | * | 11/1998 | Mann et al. | 600/523 |
| 6,418,346 | B1 | * | 7/2002 | Nelson et al. | 607/59 |
| 6,442,433 | B1 | * | 8/2002 | Linberg | 607/60 |
| 6,622,045 | B2 | * | 9/2003 | Snell et al. | 607/30 |
| 6,735,478 | B1 | * | 5/2004 | Snell | 607/59 |
| 6,804,558 | B2 | * | 10/2004 | Haller et al. | 607/30 |
| 6,987,998 | B2 | * | 1/2006 | Kalgren et al. | 600/523 |
| 2004/0049244 | A1 | * | 3/2004 | Cao et al. | 607/60 |

FOREIGN PATENT DOCUMENTS

EP    0 761 255 A1    3/1997

* cited by examiner

*Primary Examiner*—Kristen Mullen
(74) *Attorney, Agent, or Firm*—Orrick Herrington & Sutcliffe LLP

(57) ABSTRACT

A process for managing medical data in an active implantable medical device such as a pacemaker, defibrillator, cardiometer or multisite device for use of the medical data by a specialized follow-up practitioner such as a cardiologist. The process is characterized by reading by telemetry the memory data (12) of the device (10) in a patient by use of a programmer (14), memorizing in a database within the programmer the raw medical data thus read, the database having a memory field (24) containing an identifier of the patient (26), an address (28) of the follow-up practitioner such as a cardiologist or a regular practitioner ensuring the medical follow-up of the patient, as well as the aforementioned raw medical data (30), transmitting by a telematic way (36) to that follow-up practitioner, at the corresponding address, the medical data relating to the identified patient, and collecting, treating and presenting to the follow-up practitioner the medical data thus transmitted. A dedicated software (44) implemented on a microcomputer (40) at the disposal of the follow-up practitioner is used for the collection of the raw data and its treatment, processing and display for use by the follow-up practitioner.

3 Claims, 1 Drawing Sheet

MANAGING MEDICAL DATA OF AN ACTIVE IMPLANTABLE DEVICE SUCH AS A PACEMAKER, DEFIBRILLATOR, CARDIOVERTOR AND/OR MULTISITE DEVICE FOR A CARDIOLOGIST

FIELD OF THE INVENTION

The present invention is directed to "active implantable medical devices" as such devices are defined by the Jun. 20, 1990 directive 90/385/CEE of the Council of the European Communities. This definition includes pacemaker, defibrillator, cardiovertor and/or multisite devices for the treatment of the disorders of the cardiac rhythm, and neurological apparatuses, medical substance diffusion pumps, cochlear implants, implanted biological sensors, etc., as well as devices for the measurement of pH or an intra-corporeal impedance (such as the measurement of the transpulmonary impedance or the intracardiac impedance).

BACKGROUND OF THE INVENTION

Active implantable medical devices to which the present invention applies, hereinafter called "implants", comprise a data memory that can be read by means of an external programmer by telemetry techniques that are well known to persons of ordinary skill in the art. The external programmer is associated with a microcomputer, comprising a display screen, a keyboard or other input interface for the entry of control commands and data, as well as memory and associated software for data memorizing (storage) and data processing.

The practitioner who uses the programmer is generally a specialized doctor, for example, the physician who implanted the device or one who works in close co-operation with the implanting physician, oftentimes in the same hospital complex. Such a practitioner has total control over the operation of the programmer and thus direct access to the data stored in the memory of the implant, as well as the ability to read, set and modify the various "programming" controls, i.e., the commands used to modify the parameter settings and the functioning of the implant.

The starting point of the present invention is the observation that the memory of the implant contains data likely to be of interest to another practitioner (referred to herein as the "follow-up practitioner"), either another medical specialist or the regular practitioner physician who ensures the current follow-up of the patient. If one takes the example of a cardiac implant, the first practitioner (i.e., the practitioner who is the implanting physician or works with that person) is a specialized doctor known as an "electrophysiologist" or "rhythmologist", and the follow-up practitioner is a specialized doctor such as a cardiologist or the regular practitioner who ensures the current follow-up of the patient following implantation.

The cardiologist typically receives a report from the electrophysiologist, who includes interpretations related to the functioning of the implant and eventually to the heartbeat rate. However, the clinical state of the patient implies a focus on employing other parameters in particular to cure pathologies, to prescribe a medication, etc.; tasks that are specific to the cardiologist and not in the area of the electrophysiologist. It will be noted that the cardiologist has the report of the electrophysiologist and the results of the clinical examinations performed by or for the cardiologist, on which a diagnosis, such as desired changes to device operating parameters and/or prescribed medications, may be based.

However, there are certain data the knowledge of which could be interesting to help the follow-up practitioner (e.g., the cardiologist) to pose a diagnosis. This preexistent data are stored in the memory of the implant.

Generally, however the follow-up practitioner does not have a programmer that would allow him to read the memory of the implant, which would also suppose that he or she is trained to use such a programmer, apparatus that also is able to modify the programming of the implant. Moreover, the reading of the complete set of data within the memory implies a selection and analysis of that data, work that in practice makes difficult the usage of a programmer by the follow-up practitioner.

OBJECTS AND SUMMARY OF THE INVENTION

It is, therefore, an object of the invention to resolve this difficulty by proposing a process for medical data management, data which are issued from the memory of the implant, to provide the follow-up practitioner with information enabling him or her to help to pose a diagnosis or to write a prescription, without requiring the acquisition of additional equipment by the follow-up practitioner.

To this end, the present invention is broadly directed to a process for managing medical data in an implant for use by more than one practitioner. One such process is characterized by the stages of: reading by telemetry the memory data of the implant device in a patient by means of a programmer; memorizing in a database of the programmer the raw medical data thus read, the database including a memory field containing an identifier of the patient, an address of a follow-up practitioner (e.g. a cardiologist or a regular practitioner) ensuring the medical follow-up of the patient, and the aforementioned raw medical data; transmitting by a telematic way to the follow-up practitioner, at the corresponding address, the medical data relating to the identified patient; collecting, treating and presenting to the follow-up practitioner the medical data thus transmitted by means of a dedicated software implemented on a microcomputer at the disposal of the follow-up practitioner.

It will be understood to those of ordinary skill in the art that the present invention is not limited to the preferential example described here that relates to the field of cardiology (with the duality electrophysiologist/cardiologist or electrophysiologist/regular practitioner), but applies mutatis-mutandis to other medical fields implying intervening practitioner parties with distinct competences in respective fields of competence, in different places and at different times, each one needing some of the particular information contained in the implant.

BRIEF DESCRIPTION OF THE DRAWING

Other features, characteristics, and advantages of the present invention will appear to a person of ordinary skill in the art in view of the following detailed description of preferred embodiments of the present invention, made with reference to the annexed drawing FIG. 1, which schematically represents the elements used within the framework of a process in accordance with a preferred embodiment.

DETAILED DESCRIPTION OF THE INVENTION

Figure 1:
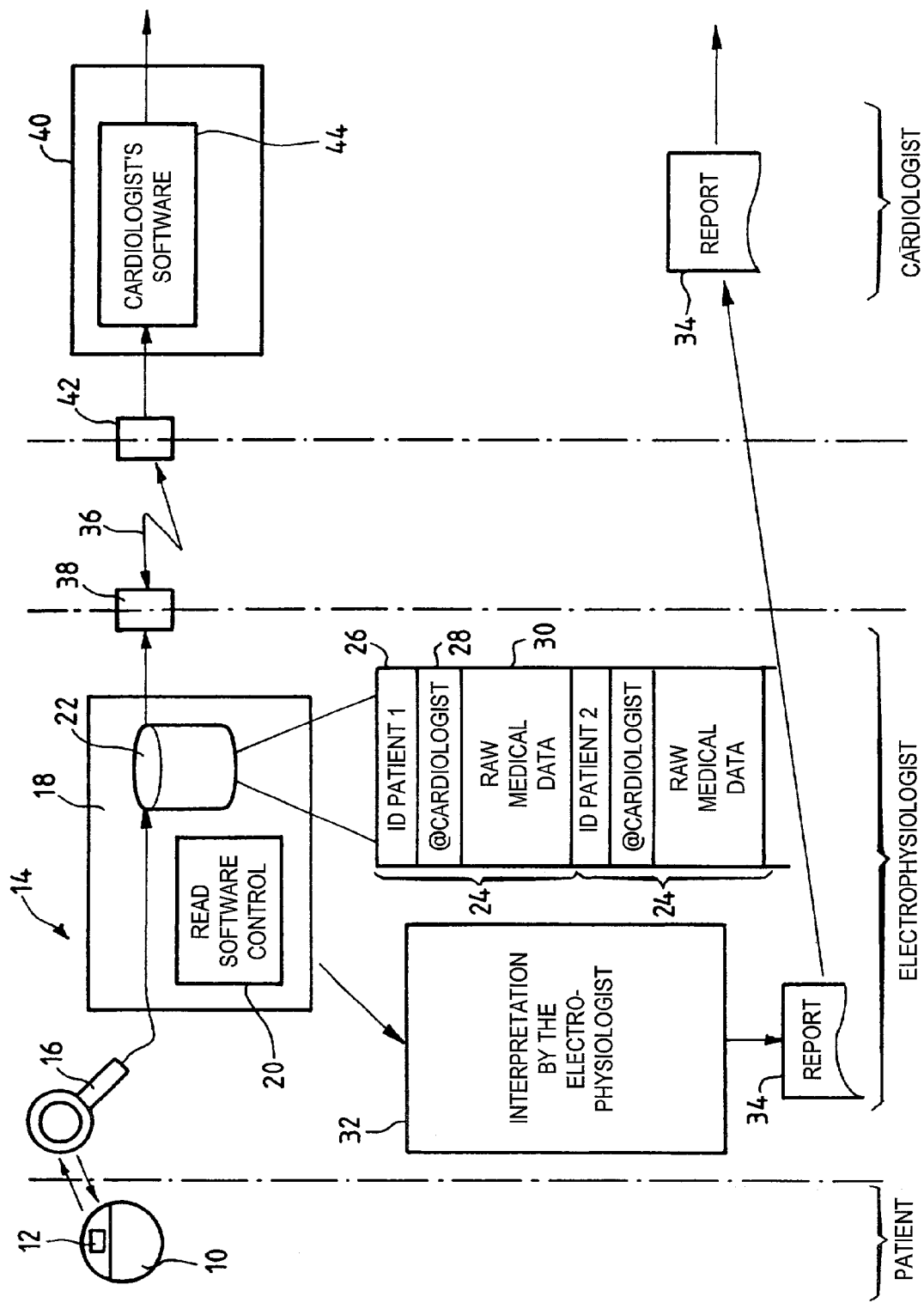

As indicated above, in particular in the field of the cardiology, the need exists to offer to the cardiologists, who look after pathologies of the patient (medication, cardiac insufficiency, etc.), but who do not control the pulse generator implant and thus do not have access to the data stored by the implant, a certain amount of information allowing them to form a diagnosis.

It will be noted that the present invention does not relate to the way in which these data are elaborated, data which preexist in the memory of the implant, nor the diagnosis itself (e.g., the significance or substance of the data or what conclusions one would draw from the data), which is posed by the follow-up practitioner using the data which are provided to him. Nor does the invention relate to other information the follow-up practitioner has on the patient and his pathology.

In the illustrated example, implant 10 is a pacemaker or a defibrillator able to store in an internal memory 12 medical data such as electrograms on the atrial or ventricular arrhythmias, the evolution of the ventilation of the patient, patient activity, a ventricular frequency, the presence of sleep apnea, the level of the stimulation capture threshold, the values of intracardiac impedance or other values, etc. This raw medical data or information is available in the memory, but until now it has been reserved to the electrophysiologist because only he has had equipment allowing one to read this data. Hence, this raw information has not been accessible to the cardiologist or the regular practitioner ensuring the current follow-up of the patient.

In order to read the data stored in memory 12 of implant 10, the electrophysiologist has a programmer 14 with a telemetry head 16 able to establish a communication with the implant 10, and a microcomputer 18 providing the various functions of processing and memorizing the data collected by the telemetry head 16. Microcomputer 18 includes in particular a software 20 for reading the data and controlling (programming) the implant, and memorizing means 22.

In a manner characteristic of the invention, when the electrophysiologist interrogates memory 12 of the implant during a control operation, the software 20 will, in addition to the usual functions, create a specific file or record comprising a plurality of zones 24 with for each one an identification field 26 of the patient, an electronic address field 28 of the cardiologist or regular practitioner ensuring the follow-up of this patient, and a field 30 storing a selection of raw medical data which could be useful within the framework of a clinical examination of the patient. These data are stored in a database in memorizing memory 22 of the programmer 14 for later use. Data for different patients will be stored in different files in the database according to the patient identifying information (e.g., an implant identification number, patient number or the like).

In addition, in a way in itself well known and traditional, the electrophysiologist carries out the work of interpretation on the disorders of the cardiac rate, the synchronization of the various cardiac cavities, etc. (work schematized by block 32). This interpretation is reduced to an establishment of a report 34, on paper and/or in electronic media, which will be addressed and delivered to the follow-up practitioner, whether a regular practitioner, a cardiologist or both.

During the next consultation of the patient, the follow-up practitioner will interrogate the database 22 via a telematic connection 36, for example, an Internet connection or a direct dial-up (modem to modem) connection or the like. For that purpose, computer 18 of the electrophysiologist is connected to this Internet connection by a corresponding modem 38 (or network ethernet link or the like, collectively hereinafter referred to as a "modem"). The follow-up practitioner can thus download the patient's raw medical data into a computer 40 at the disposal of the follow-up practitioner, typically an equipment of the current type, i.e., one that is not a dedicated programmer device, and similarly equipped with a compatible modem 42.

It will be noted that the data transmission from computer 18 of the electrophysiologist to computer 40 of the cardiologist can be done as well as on the initiative of the electrophysiologist. For example, an electronic mail message with a copy of the raw data stored in database 22 attached as a file or imbedded in the message can be sent by the electrophysiologist after the raw It will be noted that the data transmission from computer 18 of the electrophysiologist to computer 40 of the cardiologist can be done as well as en the initiative of the electrophysiologist. For example, an electronic mail message with a copy of the raw data stored in database 22 attached as a file or embedded in the message can be sent by the electrophysiologist after the raw data is acquired to each identified follow-up practitioner for each patient. In this later case, the transmission may be operated systematically during or after the consultation at the electrophysiologist's office. In an alternative embodiment a third-party service like a web host server can serve as an intermediate link between those two computers. For example, a third-party service provider can be interposed between the electrophysiologist and the cardiologist in which the third-party maintains a database replicating the contents of programmer database 22. In this embodiment, the raw data information for a given patient is uploaded by the electrophysiologist to the third-party database, where it is stored and always accessible to the cardiologist. The cardiologist can then log onto the third-party server and retrieve the patient specific data. In this way, the cardiologist need not depend on the electrophysiologist's computer 18 being running and accessible remotely.

The existence in field 28 of file 24 of the address of the cardiologist makes it possible to identify the latter and to reserve only for him the transmission of the medical data 30 which are intended for him (and conversely access to the raw data 30). The raw data thus downloaded could then be consulted and/or analyzed by the use of a dedicated software 44 loaded in computer 40, to allow, for example, a display of the medical data in the form of a table or a page-screen (not shown).

Software 44 is preferably a dedicated software for use by the cardiologists, very simple insofar as it contains only controls for remote downloading of the raw data and presentation of the raw data on the screen of the computer. From these data, as well as from the report 34 from the electrophysiologist and clinical examinations, the cardiologist will be able to benefit from having all information available on the patient in order to pose a diagnosis or write a suitable prescription.

It should be understood that the present invention is preferably implemented in software of a microprocessor controlled implantable medical device and its cooperating programmer device. Suitable implantable devices include, but are not limited to commercial pacemaker products sold under the Talent™ brand, and its associated programmer devices available from Ela Medical, Montrouge, France. These programmers contain modems and data communication programs that are capable of, or can be easily modified to respond to appropriate password protected inquiries from remote devices to allow remote access to selected data files for teletransmission to the remote computer, and alternatively or in addition, an electronic mail messaging system or file transfer system capable of generating an electronic message including the raw data for transmission to a remote device. Similarly, the follow-up practitioner's computer also will have suitable communications and electronic mail (file transfer) capabilities. The telecommunications can be via wire or wireless telephone (modem) and broadband (ethernet, cable modem or DSL) systems or networks.

Further, it is believed to be well within the abilities of a person of ordinary skill in the art to acquire and/or develop the software to be used in the follow-up practitioner's computer and in the programmer used by the first practitioner to accomplish the raw data transmission and display as discussed herein.

Advantageously, the present invention can be implemented in software instructions that perform the aforementioned functions and the software can be delivered to the appropriate devices by CD ROM and/or an electronic file transfer such as over the Internet.

One skilled in the art will appreciate that the present invention can be practiced by other than the described embodiments, which are presented for purposes of illustration and not of limitation.

We claim:

1. A process for managing medical data acquired by a memory of an active implantable medical device, comprising:

providing a programmer having a first micro-computer and a telemetry system to communicate with an active implantable medical device memory for use by an electrophysiologist, reading through telemetry medical data stored in the memory of said implantable device, creating a data file in said first micro-computer, wherein said data file comprises a first field for patient identification, a second field storing a selection of read medical data, and a third field for an electronic address of a follow-up practitioner, providing a second micro-computer, for use by said follow-up practitioner, identifying the follow-up practitioner through the corresponding electronic address field stored in the data file in the first micro-computer, downloading the selected medical data stored in said first micro-computer to said second micro-computer and exclusively to the identified follow-up practitioner, and displaying the downloaded selected medical data at said second micro-computer.

2. The process of claim 1, wherein said downloading is operated systematically after said first micro-computer acquires medical data from said active implantable medical device.

3. The process of claim 1, wherein said downloading is operated through an interrogation of the data file in first micro-computer by said follow-up practitioner.

* * * * *